United States Patent
Best, Jr. et al.

(10) Patent No.: US 6,949,085 B1
(45) Date of Patent: Sep. 27, 2005

(54) SAFETY SYRINGE ASSEMBLY

(76) Inventors: Lester Best, Jr., 3011-D S. Holden Rd., Greensboro, NC (US) 27419; John R. Powell, Jr., 911 Julian Allsbrook Hwy., Weldon, NC (US) 27890; Henry Boyd, III, 2200 Cornwallace Manor, Apartment #205, Greensboro, NC (US) 27406

( * ) Notice: Subject to any disclaimer, the term of this patent is extended or adjusted under 35 U.S.C. 154(b) by 72 days.

(21) Appl. No.: 10/366,162

(22) Filed: Feb. 13, 2003

(51) Int. Cl.$^7$ .............................................. A61M 5/32
(52) U.S. Cl. ................................................... 604/198
(58) Field of Search ..................... 604/110, 187, 192, 604/197, 198, 240

(56) References Cited

U.S. PATENT DOCUMENTS

| | | | |
|---|---|---|---|
| 2,876,770 A | 3/1959 | White | |
| 3,186,408 A | * 6/1965 | Jacob | ................. 604/240 |
| 3,749,084 A | 7/1973 | Cucchiara | |
| 4,258,713 A | 3/1981 | Wardlaw | |
| 4,507,118 A | 3/1985 | Dent | |
| 4,542,749 A | 9/1985 | Caselgrandi et al. | |
| 4,573,976 A | 3/1986 | Sampson et al. | |
| 4,581,015 A | 4/1986 | Alfano | |
| 4,643,200 A | * 2/1987 | Jennings, Jr. | ............... 600/576 |
| 4,664,654 A | 5/1987 | Strauss | |
| 4,723,943 A | 2/1988 | Spencer | |
| 4,725,267 A | 2/1988 | Vaillancourt | |
| 4,747,837 A | 5/1988 | Hauck | |
| 4,767,413 A | 8/1988 | Haber et al. | |
| 4,787,891 A | 11/1988 | Levin et al. | |
| 4,813,426 A | 3/1989 | Haber et al. | |
| 4,820,275 A | 4/1989 | Haber et al. | |
| 4,887,999 A | 12/1989 | Alles | |
| 4,908,023 A | 3/1990 | Yuen | |
| 4,909,795 A | 3/1990 | Gelabert | |
| 4,917,679 A | 4/1990 | Kronner | |
| 4,929,237 A | 5/1990 | Medway | |
| 4,932,947 A | 6/1990 | Cardwell | |
| 4,955,868 A | 9/1990 | Klein | |
| 4,958,622 A | 9/1990 | Selenke | |
| 5,024,616 A | 6/1991 | Ogle, II | |
| 5,265,621 A | 11/1993 | Simpson et al. | |
| 5,360,409 A | 11/1994 | Boyd, III et al. | |
| 5,376,080 A | 12/1994 | Petrussa | |
| 5,389,070 A | 2/1995 | Morell | |
| 5,411,487 A | * 5/1995 | Castagna | ................. 604/198 |
| 5,695,475 A | 12/1997 | Best, Jr. et al. | |
| 6,669,671 B1 | * 12/2003 | Mohammad | ................. 604/195 |

OTHER PUBLICATIONS

Tech Update, one page containing article entitled: Safe Blood Collector; author and date unknown.

* cited by examiner

*Primary Examiner*—Nicholas D. Lucchesi
*Assistant Examiner*—Mark K. Han

(57) ABSTRACT

A safety syringe assembly is provided which can be united for use and disposed thereafter in a safe manner. Accidental punctures and cross-contamination from used needles are eliminated by use of the retractable needle and removable shroud. The syringe assembly is efficient in operation, low in cost and the method of use is easily learned due to the relatively small number of syringe components employed.

18 Claims, 3 Drawing Sheets

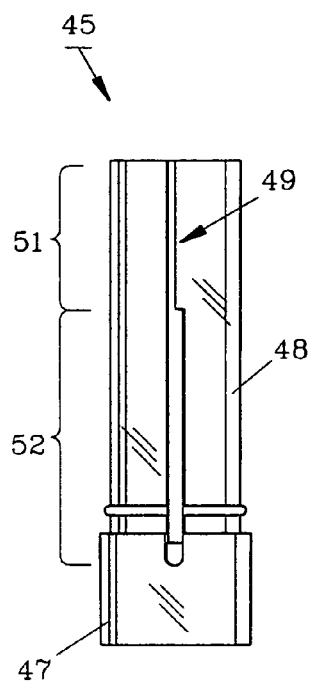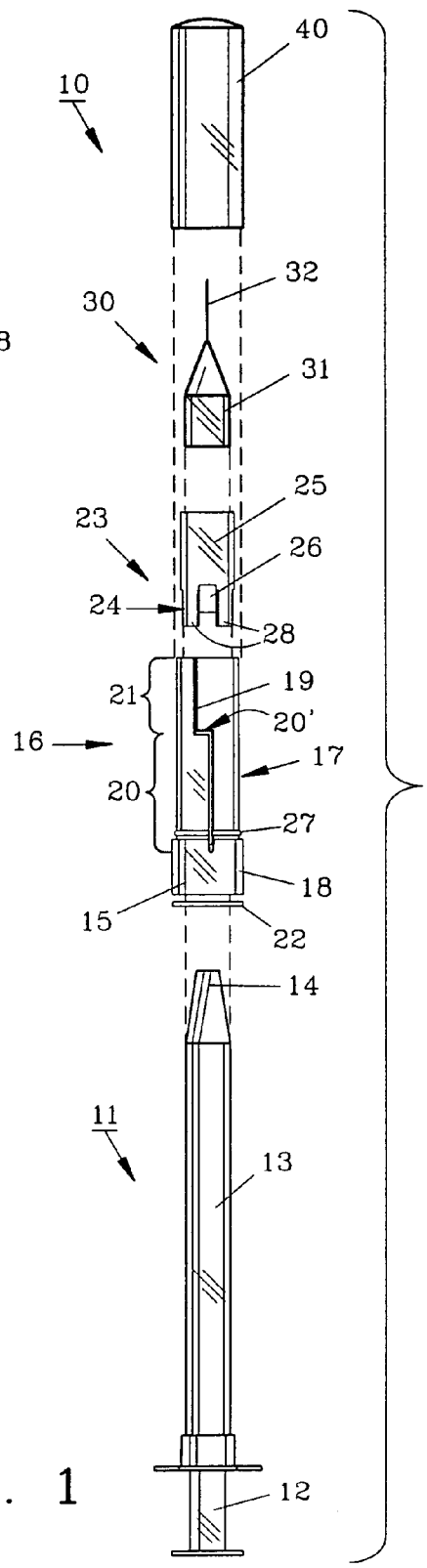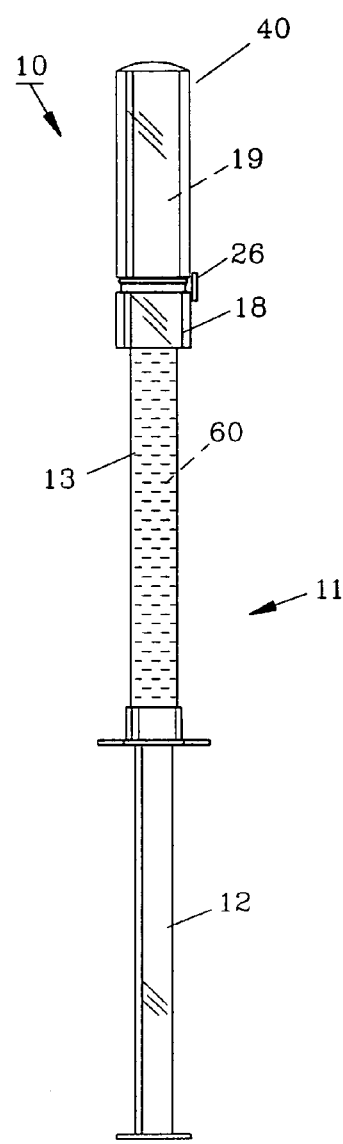
FIG. 7
FIG. 1
FIG. 2

SAFETY SYRINGE ASSEMBLY

FIELD OF THE INVENTION

The present invention pertains to syringes used in hospitals, medical offices and the like and particularly pertains to a syringe having a retractable needle to prevent inadvertent punctures and cross-infection from a contaminated needle.

DESCRIPTION OF THE PRIOR ART AND OBJECTIVES OF THE INVENTION

Many attempts have been made in the past to provide syringes with needles that are shrouded or which retract into a housing to prevent the spread of deadly diseases such as AIDS, Hepatitis and others. Certain prior safety syringe devices are complicated and expensive to manufacture, difficult to use and have generally not been well received by the public. Other prior syringe devices do not work consistently, and sometimes jam, causing problems for the healthcare personnel using them.

Thus in view of the disadvantages and problems of prior safety syringes, the present invention was conceived and one of its objectives is to provide a safety syringe assembly which can be shipped and stored in component fashion and easily united when needed for use.

It is another objective of the present invention to provide a safety syringe assembly which is relatively inexpensive to manufacture and distribute.

It is also an objective of the present invention to provide a safety syringe assembly which has relatively few moving parts, thus simplifying the manufacturing steps and limiting the chances of a malfunction.

It is yet another objective of the present invention to provide a safety syringe assembly which will provide protection for the user before, during and after syringe usage.

It is still another objective of the present invention to provide a safety syringe assembly of the disposable type.

It is yet a further objective of the present invention to provide a safety syringe assembly which utilizes a conventional syringe.

Various other objectives and advantages of the present invention will become apparent to those skilled in the art as a more detailed description is set forth below.

SUMMARY OF THE INVENTION

The aforesaid and other objectives are realized by providing a safety syringe assembly which is inexpensive to manufacture using standard injection or other molding techniques. The syringe assembly employs a conventional syringe and a conventional needle while incorporating a novel needle carriage, needle carriage housing and shroud.

The method of use includes the steps of placing a conventional syringe needle into the needle carriage and then mounting the needle carriage with needle within the carriage housing. The carriage housing includes a cylindrical sheath and base attached thereto. The preferred sheath has a z-shaped slot which accepts a tab formed on the needle carriage. The z-shaped slot allows the needle to slide in and out of the sheath and prevents inadvertent needle removal. However, the z-shaped slot can be subjected to manual (prying) pressure to allow the carriage to be inserted into the sheath during assembly or removed therefrom as required. A polymeric, sanitary rupturable seal is contained on the bottom of the housing base to maintain the needle within the carriage housing in a sanitary condition before use. When needed, the barrel of a conventional syringe is inserted through the rupturable seal to engage the receptor on the needle carriage.

To totally enclose the needle within the sheath a transparent shroud is affixed. With the shroud removed from the carriage housing the syringe can be urged upwardly, through the carriage housing thereby causing the needle shaft to extend beyond the sheath for injection or other purposes. Once the needle has been used, the needle can be retracted by urging the syringe downwardly, the shroud replaced and the syringe extracted from the receptor. Both the syringe and the shrouded carriage housing can be disposed independently, in a safe, easy manner without fear of an accidental needle puncture and possible infection from a contaminated needle.

BRIEF DESCRIPTION OF THE DRAWINGS

FIG. 1 shows a side view of the safety syringe assembly of the invention in exploded fashion;

FIG. 2 illustrates an assembled version of the safety syringe assembly shown in FIG. 1;

FIG. 7 shows an enlarged partial view of the alternate carriage housing of the alternate safety syringe assembly.

DETAILED DESCRIPTION OF THE PREFERRED EMBODIMENT AND OPERATION OF THE INVENTION

Figures 3, 4, 6:
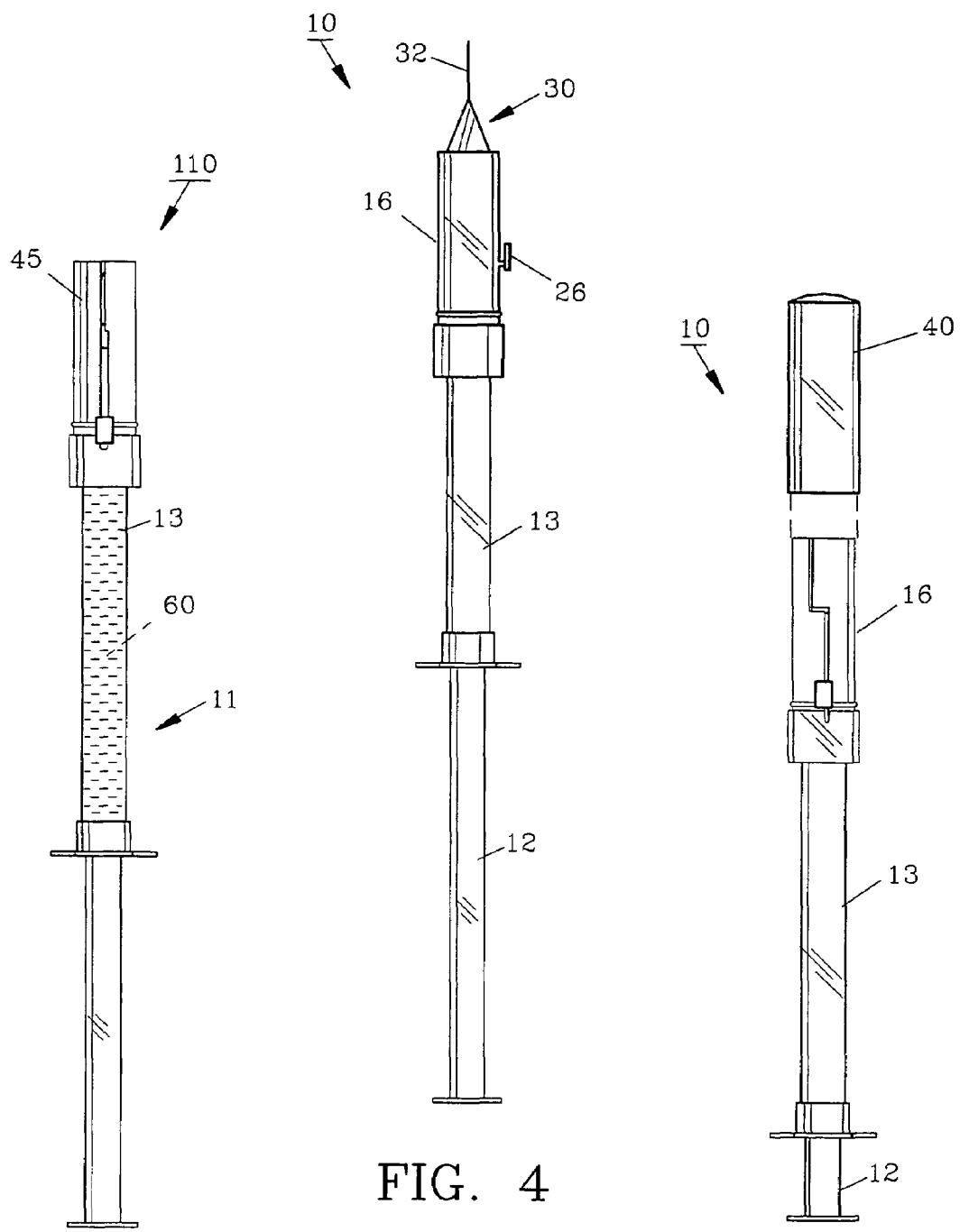
FIG. 3 demonstrates the alternate safety syringe assembly with the shroud removed from the alternate carriage housing and the needle retracted as immediately before use.
FIG. 4 pictures the safety syringe assembly as shown in FIG. 2 with the needle shaft exposed for injection purposes.
FIG. 6 demonstrates the safety syringe assembly with the shroud being replaced after use.

For a better understanding of the invention and its operation, turning now to the drawings, FIG. 1 demonstrates preferred safety syringe assembly 10 in exploded fashion with conventional disposable syringe 11 having plunger 12 and syringe barrel 13 with barrel tip 14. Carriage housing 16 is also shown and includes transparent sheath 17 affixed to base 18 by integrally molding or forming therewith. Carriage housing 16 is preferably formed from a standard polymeric material such as a suitable polycarbonate. Z-shaped tab slot 19 in sheath 17 is relatively wide along lower portion 20 for syringe usage and is narrower along upper portion 21 for assembly purposes. Lower portion 20 and upper portion 21 are relatively parallel to one another and perpendicular to slot transverse central portion 20'.

Needle carriage 23 (see FIG. 1) readily slides within sheath 17 of carriage housing 16 as tab 26 of needle carriage 23 is seen in FIGS. 2 and 4. Syringe receptor 24 is affixed to body 25 of needle carriage 23. Tab 26 is also affixed to body 25 of needle carriage 23 as by being molded therewith. Tab 26 is sized to slide within z-shaped slot 19. As slot 19 is wider along lower portion 20, tab 26 slides easily therealong. Upper portion 21 of z-shaped slot 19 is narrower but allows forced entry of tab 26 during assembly such as by manually prying upper portion 21 open with a tool such as with the blade of a small screwdriver or knife.

When needed, barrel tip 14 is urged through rupturable polymeric housing seal 22 on carriage housing 16 and frictionally engages tip receptor 24 having flexible fingers 28. Barrel 13 is sized to move through channel 15 of base 18 and sheath 17 as needle carriage 23 is urged outwardly as shown in FIG. 4. Conventional needle 30 is placed on body 25 of needle carriage 23 and is frictionally held thereon. Needle 30 is conventional and includes conical base 31 with needle shaft 32 attached.

Shroud 40, seen in FIGS. 2 and 6, is a transparent polymeric material such as a conventional polycarbonate and is of a diameter to "snap" fit over carriage housing ring 27 for frictional engagement therewith.

FIG. 2 demonstrates a view of preferred safety syringe assembly 10 in united fashion prior to use. In FIG. 3 illustrating alternate safety syringe 110, shroud 40 has been removed from alternate carriage housing 45 with injection fluid 60 contained within syringe barrel 13 which, for example may be used for a vaccination or the like. In FIG. 4, needle 30 is shown with needle shaft 32 fully exposed for injection purposes as syringe barrel 13 has been urged into carriage housing 16 as seen by the location of tab 26 at the upper most point of lower portion 20 of z-shaped slot 19.

Figure 5:
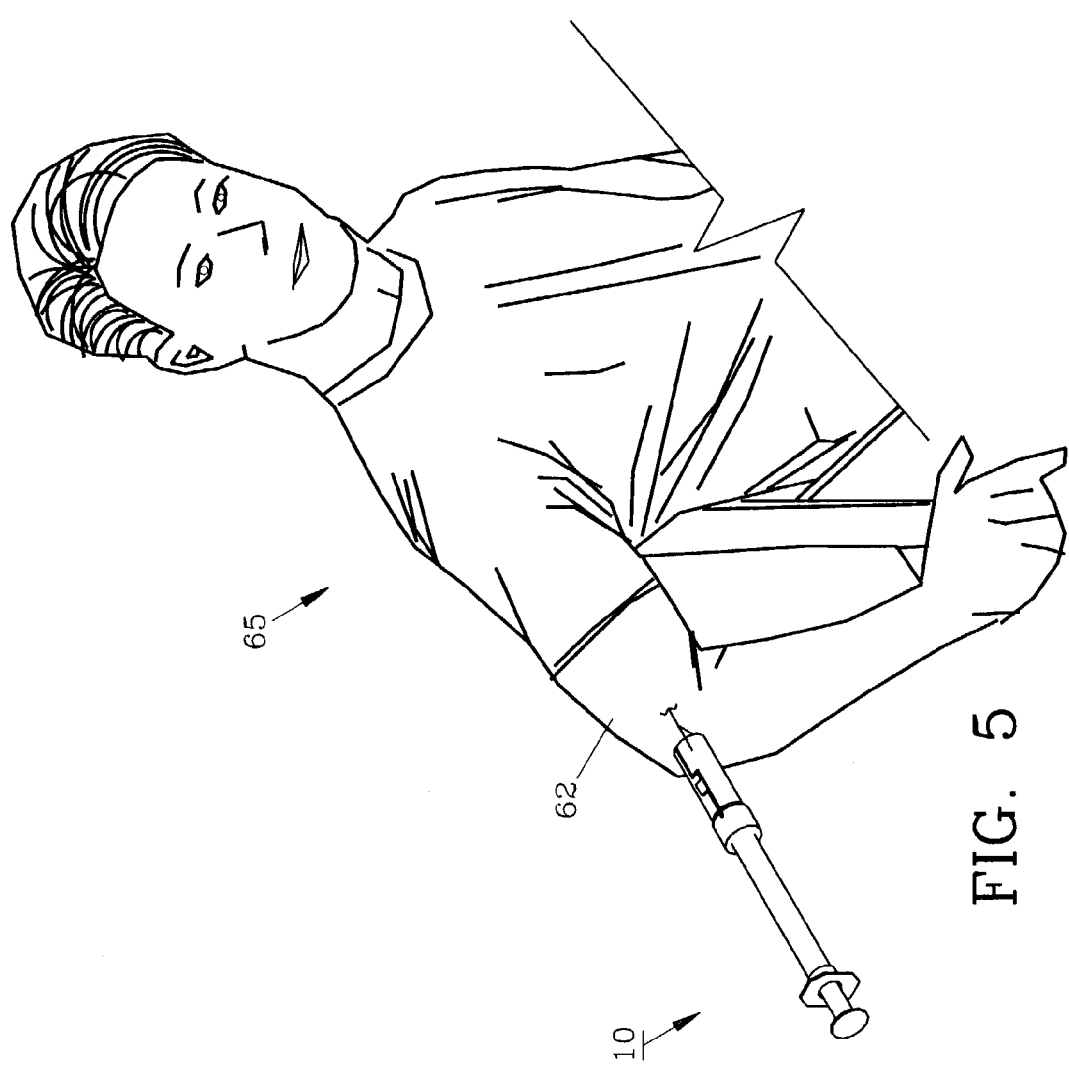
FIG. 5 illustrates an injection with the safety syringe assembly.

FIG. 5 features safety syringe assembly 10 during injection of injection fluid 60 into arm 62 of patient 65. Thereafter injection, needle 30 would be withdrawn from the arm and needle 30 retracted into carriage housing 16 to conceal needle shaft 32 such as shown in FIG. 3 with alternate carriage housing 45. Shroud 40 can then be placed on carriage housing 16 or alternate carriage housing 45 to completely and safely enclose needle 30 (see FIG. 2). Used syringe assembly 10 can then be discarded without fear of an inadvertent needle puncture of the user or others. Thus, safety syringe assembly 10 provides advantages over conventional retractable syringes with ultimate security for the user.

The method of use of preferred safety syringe assembly 10 includes the steps of frictionally affixing needle 30 to needle carriage 23 manually. Needle carriage 23 with needle 30 affixed is then positioned within carriage housing 16 by aligning tab 26 to engage upper portion 21 of slot 19 as seen in FIGS. 1 and 2. Upper slot portion 21 can then be pried or forced open to allow tab 26 to pass therealong. As tab 26 reaches the lowermost point of upper slot portion 21, needle carriage 23 is rotated in a left to right direction through central portion 20' as seen in FIG. 1 whereby tab 26 then enters wider, lower slot portion 20 and descends toward base 18. Shroud 40 is then placed over housing sheath 17 and with slight finger pressure, shroud 40 "snaps" onto housing ring 27 where it is maintained until removal. Thus, carriage housing 16 containing needle 30 with shroud 40 attached can then be distributed as one component along with conventional syringe 11 as another component to potential users.

Another alternate embodiment of the carriage housing is enlarged in FIG. 7. As shown, carriage housing 45 includes base 47 and sheath 48, integrally formed from a transparent polymeric material such as a polycarbonate. Slot 49 has a different shape than z-shaped slot 19 of preferred carriage housing 16. As seen, slot 49 includes wider, lower slot portion 52 and narrower, upper slot portion 51. Slot portion 51 must by pried or forced open to allow carriage tab 26 (not seen in FIG. 7) to pass therealong during assembly.

A potential user such as a healthcare worker, nurse or others can then simply remove carriage housing 16 from its shipping container and with shroud 40 still in place, urge barrel tip 14 of syringe 11 through rupturable housing seal 22. Tip 14 then engages fingers 28 of tip receptor 24 in a frictionally tight manner. Shroud 40 can then be removed from carriage housing 16 and by urging syringe 11 upwardly (as seen in FIG. 1) through base 18, needle shaft 32 is then exposed. Needle shaft 32 could then be inserted into a typical vaccine bottle or the like (not shown) and by withdrawing plunger 12, barrel 13 would fill with vaccine or other fluid.

Once barrel 13 is filled, syringe 11 can be urged downwardly through base 18 of carriage housing 16 to withdraw needle 30 into sheath 17. Shroud 40 can then be replaced and syringe assembly 11 is then available for injection purposes. As needed, shroud 40 can be removed, syringe 11 urged upwardly through base 18 of carriage 16 to expose needle 32. As shown in FIG. 5, an injection into arm 62 can easily be made and thereafter syringe 11 can again be withdrawn through base 18 whereupon needle 30 is then retracted into housing sheath 17. Shroud 40 can be repositioned over sheath 17, thereby allowing syringe 11 to be totally removed from tip receptor 24 and carriage housing 16 for disposal purposes. Likewise, carriage housing 16 and needle 30 contained therein with shroud 40 attached can be properly disposed. As thus described, needle 30 can be retracted within carriage housing 16 after use and fully enclosed by engaging shroud 40.

The illustrations and examples provided herein are for explanatory purposes and are not intended to limit the scope of the appended claims.

We claim:

1. A safety syringe assembly comprising: a syringe, a needle carriage, said needle carriage defining flexible fingers, said fingers frictionally engaging said syringe, a carriage housing, said needle carriage slidable within said carriage housing, a needle, said needle attached to said needle carriage whereby said needle carriage can be slid upwardly within said carriage housing to expose said needle for injection purposes and can be slid towards said carriage housing to conceal said needle.

2. The safety syringe assembly of claim 1 further comprising a shroud, said shroud removably positioned on said carriage housing, said carriage housing defining a housing ring, said shroud frictionally engageable with said housing ring.

3. The safety syringe assembly of claim 1 wherein said syringe is disposable.

4. The safety syringe assembly of claim 1 wherein said carriage housing defines a central channel, a rupturable seal, said seal covering said central channel whereby said syringe penetrates said seal for entry into said central channel.

5. The safety syringe assembly of claim 1 wherein said carriage housing comprises a base, a sheath, said sheath attached to said base, said sheath defining a slot, said needle carriage comprising a tab, said tab slidably positioned within said slot.

6. The safety syringe assembly of claim 5 wherein said slot is z-shaped, said slot having a transverse central portion, an axial upper portion, and an axial lower portion, said central portion positioned between said upper and said lower portions, said lower portion in communication with said central portion, said upper portion in communication with said central portion, said upper and said lower portions parallel to one another, said central portion perpendicular to said upper portion.

7. The safety syringe assembly of claim 1 formed from polymeric materials.

8. The safety syringe assembly of claim 1 wherein said needle carriage comprises a body, a syringe receptor, said syringe receptor attached to said body, said syringe receptor defining said fingers, and a tab, said tab affixed to said body.

9. The safety syringe assembly of claim 1 wherein said syringe comprises a tip, said tip for insertion into said syringe receptor.

10. A safety syringe assembly comprising: a syringe, said syringe comprising a barrel, a plunger, said plunger contained within said barrel, said barrel defining a tip, a needle carriage, a needle, said needle mounted on said needle carriage, a carriage housing, said needle carriage slidably contained within said carriage housing, said needle carriage defining a syringe receptor, said barrel tip frictionally positioned within said syringe receptor, a shroud, said shroud releasably positioned on said carriage housing, said carriage housing defining a housing ring, said shroud frictionally engaged by said housing ring, a rupturable seal, said seal positioned on said carriage housing, said seal sized to receive said barrel when ruptured, whereby said needle can be extended from said carriage housing for providing injections and retracted therewithin for safety purposes.

11. The safety syringe assembly of claim 10 wherein said needle carriage housing defines a slot, said needle carriage comprising a tab, said tab slidably positioned within said slot.

12. The safety syringe assembly of claim 10 wherein said needle carriage further defines flexible fingers on said syringe receptor.

13. The safety syringe assembly of claim 10 formed from a polymeric material.

14. The safety syringe assembly of claim 11 wherein said carriage housing slot is z-shaped.

15. The safety syringe assembly of claim 10 further comprising a carriage housing base, a carriage sheath, said sheath attached to said carriage housing base.

16. The safety syringe assembly of claim 15 wherein said seal is affixed to said carriage housing base.

17. A safety syringe assembly for a conventional syringe comprising: a needle carriage, said needle carriage comprising a body, a syringe receptor, said syringe receptor attached to said body, and a tab, said tab affixed to said body, said syringe receptor defining flexible fingers, said fingers frictionally engageable with the syringe, a needle, said needle frictionally attached to said needle carriage, a carriage housing, said carriage housing comprising a base, and a sheath, said sheath attached to said base, said sheath defining a slot and a housing ring, said tab slideably positioned within said slot, said housing ring contiguous said base, said carriage housing defining a central channel, a rupturable seal, said seal positioned over said central channel contiguous said base, said central channel sized to receive the syringe, said needle carriage slideably positioned within said central channel whereby said needle housing can be slid away from said base to expose said needle for injection purposes and slid towards said base to conceal said needle within said housing carriage for safety purposes and the syringe can pierce said seal and be received by said syringe receiver within said central channel.

18. The safety syringe assembly of claim 17 further comprising a shroud, said shroud removeably positioned on said carriage housing, said shroud frictionally engageable with said housing ring whereby said shroud is removed before extending said needle from said carriage housing.

* * * * *